United States Patent [19]
Wang et al.

[11] Patent Number: 5,500,181
[45] Date of Patent: Mar. 19, 1996

[54] SHRINKING BALLOON CATHETER HAVING NONLINEAR COMPLIANCE CURVE

[75] Inventors: Lixiao Wang, St. Paul; The T. T. Tran, Coon Rapids, both of Minn.

[73] Assignee: Scimed Life Systems, Inc., Maple Grove, Minn.

[21] Appl. No.: 380,607

[22] Filed: Jan. 3, 1995

Related U.S. Application Data

[62] Division of Ser. No. 245,372, May 18, 1994, Pat. No. 5,403,340, which is a division of Ser. No. 953,677, Sep. 29, 1992, Pat. No. 5,348,538.

[51] Int. Cl.$^6$ ............................ B29C 49/04; B29C 49/14
[52] U.S. Cl. ...................... 264/532; 264/573; 264/909; 604/96; 606/194
[58] Field of Search ..................... 604/96; 606/192, 606/194; 264/523, 523, 570, 573, 900, 909

[56] References Cited

U.S. PATENT DOCUMENTS

| | | |
|---|---|---|
| Re. 32,983 | 7/1989 | Levy . |
| Re. 33,561 | 3/1991 | Levy . |
| 2,995,779 | 8/1961 | Winter . |
| 3,088,173 | 5/1963 | Jones . |
| 3,141,912 | 7/1964 | Goldman et al. . |
| 3,317,642 | 5/1967 | Bailey ........................................ 264/900 |
| 3,432,591 | 3/1969 | Heffelfinger . |
| 3,627,579 | 12/1971 | Heffelfinger . |
| 3,733,309 | 5/1973 | Wyeth et al. . |
| 3,865,666 | 2/1975 | Shoney . |
| 3,908,201 | 1/1976 | Jones et al. . |
| 3,959,200 | 5/1976 | Scott . |
| 4,093,484 | 6/1978 | Harrison et al. . |
| 4,154,244 | 5/1979 | Becker et al. . |
| 4,254,774 | 3/1981 | Boretos . |
| 4,256,789 | 3/1981 | Suzuki et al. . |
| 4,367,747 | 1/1983 | Witzel . |
| 4,387,833 | 6/1983 | Venus, Jr. . |
| 4,411,055 | 10/1983 | Simpson et al. . |
| 4,413,989 | 11/1983 | Schjeldahl et al. . |
| 4,456,000 | 6/1984 | Schjeldahl et al. . |

(List continued on next page.)

FOREIGN PATENT DOCUMENTS

| | | |
|---|---|---|
| 0135990 | 4/1985 | European Pat. Off. . |
| 174263 | 3/1986 | European Pat. Off. ............... 264/900 |
| 0186267 | 7/1986 | European Pat. Off. . |
| 0197787 | 10/1986 | European Pat. Off. . |
| 274411 | 7/1988 | European Pat. Off. . |
| 0345051 | 12/1989 | European Pat. Off. . |
| 0355937 | 2/1990 | European Pat. Off. . |
| 0362826 | 4/1990 | European Pat. Off. . |
| 485903 | 5/1992 | European Pat. Off. . |
| 0492361 | 7/1992 | European Pat. Off. . |
| 540858 | 5/1993 | European Pat. Off. . |
| 582870 | 7/1993 | European Pat. Off. . |
| 420488 | 7/1993 | European Pat. Off. . |
| WO89/08473 | 9/1989 | WIPO . |
| WO92/08512 | 5/1992 | WIPO . |
| 19440 | 11/1992 | WIPO . |

OTHER PUBLICATIONS

Effect Of Inflation Pressures On Coronary Angioplasty Balloosn, Avanindra Jain, MD;, Linda L. Demer, MD; Albert E. Raizner, MD; and Robert Roerts, MD. (AM J Cardiol 1986; 57:26–28).

(List continued on next page.)

*Primary Examiner*—Catherine Timm
*Attorney, Agent, or Firm*—Vidas, Arrett & Steinkraus

[57] ABSTRACT

A balloon catheter, having a non-linear compliance curve, made up of a single layered balloon, that was molded from a polymeric material to have a specific nominal diameter and then shrunk to a diameter that is less than the specific nominal diameter. When the shrunk balloon is expanded it has the characteristics of a compliant balloon until its diameter has been expanded to its original specific nominal diameter after which it follows the non compliant compliance curve that it would have had it not been shrunk.

9 Claims, 4 Drawing Sheets

U.S. PATENT DOCUMENTS

| | | | |
|---|---|---|---|
| 4,482,518 | 11/1984 | Brady, Jr. | 264/900 |
| 4,490,421 | 12/1984 | Levy. | |
| 4,531,943 | 7/1985 | Van Tassel et al. | |
| 4,531,997 | 7/1985 | Johnston. | |
| 4,587,975 | 5/1986 | Salo et al. | |
| 4,608,984 | 9/1986 | Fogarty. | |
| 4,637,396 | 1/1987 | Cook. | |
| 4,646,742 | 3/1987 | Packard et al. | |
| 4,743,258 | 5/1988 | Ikada et al. | |
| 4,807,619 | 2/1989 | Dyrud et al. | |
| 4,884,573 | 12/1989 | Wijay et al. | |
| 4,906,241 | 3/1990 | Noddin et al. | 606/194 |
| 4,906,244 | 3/1990 | Pinchuk et al. | |
| 4,932,945 | 6/1990 | Reddy et al. | |
| 4,938,676 | 7/1990 | Jackowski et al. | |
| 4,941,877 | 7/1990 | Montano, Jr. | |
| 4,950,239 | 8/1990 | Gahara et al. | |
| 4,952,357 | 8/1990 | Euteneuer. | |
| 4,963,313 | 10/1990 | Noddin et al. | |
| 5,015,230 | 5/1991 | Martin et al. | 606/194 |
| 5,087,394 | 2/1992 | Keith. | |
| 5,156,612 | 10/1992 | Pinchuk et al. | |
| 5,290,306 | 3/1994 | Trotta et al. | |
| 5,306,246 | 4/1994 | Sahatjian et al. | 604/96 |

OTHER PUBLICATIONS

Adams, D. O., "PTCA Balloon Materials, Their Characteristics And Impact On Catheter Selection".

P. Chandran and S. A. Jabarin, "Biaxial Orientation of Poly(Ethylene Terephthalate)," pp. 880–885, ANTEC '91.

P. Tugcu, K. W. Neale and A. Marquez–Lucero, "Effect of Deformation–Induced Heating on the Cold Drawing of Polymeric Films," pp. 104–111, Jan. 1991, *Journal of Engineering Materials and Technology.*

M. Cakmak, Y. D. Wang, and M. Simhambhatla, "Processing Characteristics, Struture Development, and Properties of Uni and Biaxially Stretched Poly(Ethylene 2,6 Naphthalate) (PEN) Films," pp. 721–733, Jun. 1990, *Polymer Engineering and Science*, vol. 30, No. 12.

S. A. Jabarin, "Crystallization Behavior of Poly(Ethylene Terephthalate)," pp. 1259–1264, Sep. 1989, *Polymer Engineering and Science*, vol. 29, No. 18.

Jiayu Guan, Wei Wu, Xiaoli Zhang, Zimian Ma & Mao Xu, "Influence of Molecular Weight on the Tensile Behaviour of PET Films Under Biaxial Stretching," pp. 23–27, 1989, *Plastics and Rubber Processing and Applications*, vol. 11, No. 1.

"Cleartuf 7407," The Goodyear Tire & Rubber Company, (Advertisement), 1989.

Schneider Shiley, "Presenting An Inflated View Of A Systematic Approach to Peripheral Angioplasty," (Advertisement), Nov. 1987.

S. A. Jabarin, "Crystallization Kinetics of Polyethylene Terephthalate I. Isothermal Crystallization From the Melt," pp. 85–96, 1987, *Journal of Applied Polymer Science*, vol. 34.

M. F. Vallat and D. J. Plazek, "Effects of Thermal Treatment of Biaxially Oriented Poly(ethylene terephthalate)," pp. 2123–2134, 1986, *Journal of Polymer Science: Part B: Polymer Physics*, vol. 24.

Frank P. Leigner, "Free–blown PET preforms characterize blown bottles," pp. 47–51, Jun. 1985, *Plastics Engineering.*

Frank P. Leigner, "Freeblowing PET Preforms," pp. 907–915, 1985, *ANTEC '85.*

R. T. Bailey, F. R. Cruickshank, A. McLeod, D. Pugh and A. G. Faraday, "Thermal lens measurements of thermal conductivity and orientation in polyethylene terephalate," pp. 23–25, Jan. 1985, *Polymer Communications*, vol. 26.

Takaka Terada, Chie Sawatari, Toyoko Chigono and Masaru Matsuo, "Oriented Crystallization of Poly(ethylene terephthalate) under Uniaxial Stretching," 1982, *American Chemical Society.*

G. S. Kirshenbaum and J. M. Rhodes, "Thermoplastic polyester: PET," pp. 50–51, 1981–1982, *Modern Plastics Encyclopedia.*

C. Bonnebat, G. Roullet and A. J. deVries, "Biaxially Oriented Poly(Ethylene Terephthalate) Bottles: Effects of Resin Molecular Weight on Parison Stretching Behavior," pp. 189–195, Mar. 1981, *Polymer Engineering And Science*, vol. 21, No. 4.

G. Hinrichsen, A. Eberhardt, U. Lippe, and H. Springer, "Orientation mechanisms during biaxial drawing of polymer films," pp. 73–79, 1981, *Colloid & Polymer Science*, vol. 259, No. 1.

B. J. Jungnickel, "Analysis Of The Degree Of Orientation Of Biaxially Drawn Polyethylene Terephthalate Foils," 1980, *Progr. Colloid Polym. Sci.*, 67, 159–60, (3 page translation).

Bruce F. Blumentritt, "Anisotropy and Dimensional Stability of Biaxially Oriented Poly(ethylene Terephthalate) Films", pp. 3205–3217, 1979, *Journal of Applied Polymer Science*, vol. 23.

R. B. Fredrickson, "Stretch–Blow Molding for Packaging Versatility," pp. 22–26, Nov. 1979, *Plastics Design & Processing.*

Andreas R. Grontzig, Ake Senning, and Walter E. Siegenthaler, "Nonoperative Dilation of Coronary–Artery Stenosis–Percutaneous Transluminal Coronary Angioplasty," pp. 61–68, Jul. 12, 1979, *The New England Journal of Medicine*, vol. 301, No. 2.

C. Shriver, "How to Reheat Blow Mold PET Soft Drink Bottles," pp. 91–93, Oct. 1977 (journal unknown).

Daniel D. Ray, Clem B. Shriver and Robert J. Garland, "Here's Why Polyethylene Terephthalate Is the Major Competitor For Beverage Container Applications," pp. 47–50, Sep. 1977, *Plastics Design & Processing.*

Raymond B. Seymour, "The Narrowing Field of Plastics For Blow Molded Beverage Containers," pp. 61–65, Jun. 1977, *Plastics Design & Processing.*

D. V. Rosato, "Processing PET," pp. 545–553, *Polyethylene Terephthalate (PET)* (date unknown).

Yoshinori Nakamura, "PET stretch–blowing–Application Development and Improvement of Product Quality," pp. 14–22, *Japan Plastics Age* (date unknown).

Saleh A. Jabarin and Elizabeth A. Lofgren, "Effects of Water Absorption on Physical Properties and Degree of Molecular Orientation of Poly(Ethylene Terephthalate)," 6 pages (date and journal unknown).

P. R. Ajmera and N. R. Schott, "Elevated Temperature Tensile Properties of Biaxially oriented PET and PET/PETG Blends," pp. 710–712 (date and journal unknown).

Kahn et al., "Inflation Pressure Requirements During Coronary Angioplasty." *Catherization and Cardiovascular Diagnosis,* 21:144–147 (1990).

Dupont Industry News, Du Pont Company/Marketing Communications Department/ Wilmington, Delaware 19898.

SHRINKING BALLOON CATHETER HAVING NONLINEAR COMPLIANCE CURVE

This application is a division of U.S. application Ser. No. 08/245,372, filed May 18, 1994, now U.S. Pat. No. 5,403,340, which is a division of U.S. application Ser. No. 07/953,677, filed Sep. 29, 1992, now U.S. Pat. No. 5,348,538.

BACKGROUND OF THE INVENTION

The present invention relates generally to balloon catheters used for angioplasty.

Angioplasty, an accepted and well known medical practice involves inserting a balloon catheter into the blood vessel of a patient, maneuvering and steering the catheter through the patient's vessels to the site of the lesion with the balloon in an un-inflated form. The un-inflated balloon portion of the catheter is located within the blood vessel such that it crosses the lesion or reduced area. Pressurized inflation fluid is metered to the inflatable balloon through a lumen formed in the catheter to thus dilate the restricted area. The inflation fluid is generally a liquid and is applied at relatively high pressures, usually in the area of six to twelve atmospheres. As the balloon is inflated it expands and forces open the previously closed area of the blood vessel. Balloons used in angioplasty procedures such as this are generally fabricated by molding and have predetermined design dimensions such as length, wall thickness and nominal diameter. Balloon catheters are also used in other systems of the body for example the prostate and the urethra. Balloon catheters come in a large range of sizes and must be suitably dimensioned for their intended use.

The term, low pressure diameter, as used herein with reference to the balloon catheter, means the diameter of the balloon when it is inflated to two (2) atmospheres.

The term, expanded diameter, as used herein with reference to the balloon catheter, means the diameter of the balloon when it is inflated to six (6) to (12) atmospheres.

All angioplasty balloons have a minimum pressure at which they will burst called the minimum burst pressure. The physician is aware of the minimum burst pressure of angioplasty balloons that he or she uses and usually avoids inflating a balloon to the point where it bursts. The physician is also aware that each kind and size of angioplasty balloon has its own expansion characteristics. This characteristic is usually expressed as a number which is the decimal portion of a millimeter that the balloon will expand when one additional atmosphere of pressure is applied. For example a 3 millimeter (low pressure diameter) balloon may expand 0.10 millimeters for each additional atmosphere of pressure that is applied. In this example at 12 atmospheres of pressure the balloon would have a diameter of 4.00 millimeters. This stretching characteristic is a factor of both the wall thickness and the material from which the balloon is molded. If the diameter of a balloon is measured during inflation, and the diameter is plotted, as one coordinate, against the inflation pressure as the other coordinate, the resulting curve is called the compliance curve for that particular balloon. If a balloon is made of a material that results in a relatively large increase in diameter when the balloon is inflated to its expanded diameter, such a balloon is said to be a High-Compliant balloon, or is said to be a balloon with a high compliance curve.

FIG. 1A, is a graph showing a set of compliance curves for catheter balloons. In FIG. 1A the inflation pressure, measured in atmospheres, is plotted along the X-axis and the balloon diameter measured in millimeters is plotted along the Y-axis. In this figure the compliance curve having the greatest inclination is labeled High-Compliant. A High-Compliant balloon has a relatively large increase in diameter in response to an increase in inflation pressure. It should be noted that balloons defined herein as High-Compliant balloons are commonly referred to in the trade as, "Compliant balloons" or balloons made from compliant plastic material.

If a balloon is made of a material that results in a relatively small increase in diameter when the balloon is inflated to its expanded diameter, such a balloon is said to be a Non-Compliant balloon, a balloon made from non compliant plastic material or a balloon with a low compliance curve. In FIG. 1A, the compliance curve having the least inclination is labeled Non-Compliant. A Non-Compliant balloon has a relatively small increase in diameter in response to an increase in inflation pressure. In FIG. 1A the third compliance curve is labeled Intermediate Compliant and represents a balloon having compliant characteristics between High and Non-Compliant balloons. It should be noted that although only three compliance curves are shown in FIG. 1A, balloons having compliant anywhere between the High-Compliant and the Non-Compliant curves are available. It should also be noted that all compliance curves shown in FIG. 1A are linear (straight lines).

High-Compliant balloons are made from relatively soft or flexible polymeric materials. Examples of these materials are thermoplastic polymers, thermoplastic elastomers, polyethylene (high density, low density, intermediate density, linear low density), various copolymers and blends of polyethylene, ionomers, polyesters, polyurethanes, polycarbonates, polyamides, polyvinyl chloride, acrylonitrile-butadiene-styrene copolymers, polyether-polyester copolymers, and polyether-polyamide copolymers. A suitable copolymer material, polyolefin material is available from E. I. DuPont de Nemours and Co. (Wilmington, Del.), under the trade name Surlyn® Ionomer.

Intermediate-Compliant balloons are made of polyethylene and nylon materials.

Non-Compliant balloons are made from relatively rigid or stiff polymeric materials. These materials are thermoplastic polymers and thermoset polymeric materials. Some examples of such materials are poly(ethylene terephthalate), polyimide, thermoplastic polyimide, polyamides, polyesters, polycarbonates, polyphenylene sulfides, polypropylene and rigid polyurethanes. Non-Compliant balloons made from poly(ethylene terephthalate) are commonly referred to as PET balloons.

The compliant characteristics of an angioplasty balloon affects how the physician uses the balloon catheter. A Non-Compliant balloon, will increase in diameter by a maximum of 1–15% of its nominal diameter in response to increasing the pressure to as much as twenty atmospheres. Sixteen atmospheres is safely below the burst pressure of such a Non-Compliant balloon. However, when inflated to its expanded diameter, a Non-Compliant balloon becomes very hard.

When a physician encounters a lesion that has become calcified and is very hard and rigid he may select a Non-Compliant balloon, that will become very hard and function to crack the rigid calcified lesion. Non-Compliant balloons have the advantage over Compliant balloons in that they can be used to dilate and crack hard lesions. Also if a Non-Compliant balloon is located in a vessel, across a restricted area of the vessel, and an end or both ends extend into non restricted areas of the vessel, the pressure in the balloon can be increased in the balloon sufficient to dilate or crack the restricted area without risking the possibility of damaging adjacent non restricted portions of the vessel. Non-Compliant balloons have the disadvantage that they are not effective if the normal vessel size lies between the size range of the available Non-Compliant balloons. Another disadvantage of Non-Compliant balloons is that if the lesion or restriction recoils after being dilated to its desired diameter, the Non-Compliant balloon cannot be used to dilate the lesion or restriction to a diameter greater than the previous dilation to thus overcome the recoil.

A High-Compliant balloon, will increase in diameter 15% to 40% in response to increasing the inflation pressure to a point safely below its burst pressure. The advantage of a High-Compliant balloon over a Non-Compliant balloon is that fewer models of High-Compliant balloons are required to fill a range of sizes. Non-Compliant balloons are typically available in size increments of 0.25 mm while High-Compliant balloons typically have size increments of 0.50 mm. Also an off-sized artery (i.e. 2.90 mm) will be difficult to dilate with a Non-Compliant balloon. Another advantage of a High-Compliant balloon over a Non-Compliant balloon is that if a restriction, after being dilated to its desired diameter, recoils when the balloon is deflated, the High-Compliant balloon can be re-inflated to a higher pressure thus dilating the restriction to a diameter greater than its desired diameter resulting in a satisfactory post recoil lumen diameter. This process can be repeated until the restriction retains its desired diameter after deflation of the balloon. High-Compliant balloons also have disadvantages, for example they can not be successfully used to dilate a hard lesion. Also if a High-Compliant balloon is located across a restriction and an end or both ends of the balloon extend into non restricted areas, when high pressure is applied to the balloon, the pressure may not be sufficient to crack or dilate the restrict area but will dilate the non restricted area to diameters greater than their normal diameter. In this situation damage can be done to the non restricted portions of the vessel.

Compliance curves of angioplasty balloons, in their usable range are linear, that is essentially a straight line. As a result a physicians choice, in the past, has been to select a balloon having a linear compliance curve that best meets his needs. Physicians often encounter medical situations where an angioplasty balloon having a nonlinear compliance curve is called for but balloon catheters with the desired compliance curve have not been available. For example a physician may have a medical situation in which he desires a balloon that will during the initial inflation phase increase in diameter by 20% and then in the secondary inflation phase become very rigid and hard with little further increase in diameter. Another example would be the situation where two lesions are encountered, one that can be treated with a High-Compliant balloon and the other that requires a Non-Compliant balloon.

The prior art discloses balloon catheters and methods for making balloon catheters in which the balloons have linear compliance curves. Reference may be had to U.S. Pat. No. 4,456,000 and reissue U.S. Pat. Nos. 32,983 and 33,561 for disclosures of methods for making balloon catheters having linear compliance curves.

In some situations a physician may desire a High-Compliant balloon that can initially expanded a significant amounts. If after the blood vessel adjacent to the restriction has been dilated to its natural size or at most 10% larger than its natural size, and the lesion has not yielded completely, it is not desirable that the balloon size be further increased due to the high rate of restenosis and dissection. In a situation such as this the physician may, after the restriction has not yielded sufficiently with the High-Compliant balloon, desire to remove the High-Compliant balloon and replace it with a Non-Compliant balloon. The Non-Compliant balloon that would be selected in this situation would have a nominal diameter approximately equal to the natural diameter of the open blood vessel, and its desired function would be to tightly compress the lesion into the wall of the blood vessel. It is desirable in this situation that the inflated balloon becomes very hard and rigid but not expand to a diameter that is greater than the natural diameter of the blood vessel. To accomplish this with currently available balloon catheters the initial High-Compliant balloon must be removed and replaced with a Non-Compliant balloon. This has the disadvantage that the patient is exposed to the trauma of removing and replacing a balloon catheter, the procedure time is lengthened and there is the expense of two balloon catheters. These disadvantages can be avoided by use of a balloon catheter that has a nonlinear or hybrid compliance curve.

A hybrid compliant balloon is a balloon that has a nonlinear or hybrid compliance curve. A benefit of a hybrid compliant balloon is that advantages of both the Compliant and Non-Compliant balloons can be obtained in a single catheter that can be sized to the artery by varying the inflation pressure.

FIG. 2A is a graph in which the balloon diameter, in millimeters, is plotted along the Y-axis and the pressure in atmospheres is plotted along the X-axis. FIG. 2A, shows the compliance curves for two particular balloon catheters. In this figure the compliance curve having the greatest inclination is labeled High-Compliant and the compliance curve having the lesser inclination is labeled Non-Compliant. A hybrid balloon combines these two compliance curves and the result is as shown by the full line compliance curve in FIG. 2A. The full line compliance curve of FIG. 2A is a non linear compliance curve which is a hybrid of the compliance curves of a compliant and a non compliant balloon.

A balloon catheter having a hybrid compliant curve is disclosed and claimed in commonly owned and pending application Ser. No. 07/927,062, filed Aug. 6, 1992, the disclosure of which is incorporated herein by reference.

In the above referred to copending application a double layered balloon is used to attain the hybrid compliance curve. The term "profile" as used with reference to balloon catheters refers to the diameter of the dilating element or balloon when it is un-inflated. Usually an un-inflated balloon will be folded down to minimize its diameter or profile. A small profile enables the balloon catheter to be manipulated through restrictions and around sharp curves. Unless the dilating element of a balloon catheter can reach and extend through tightly closed lesion it cannot perform its task of dilating the lesions or restriction. A double layered balloon will have a larger profile than a comparable single layered balloon. Although a double layered balloon increases the profile of a balloon catheter, having a hybrid compliance curve outweigh the disadvantages of the increased profile. However a single layered balloon catheter that has a hybrid compliance curve is even more advantageous.

The stiffness or flexibility of the un-inflated dilating element or balloon portion of a balloon catheter is another factor contributing to the maneuverability of a balloon catheter. The more flexible the balloon section is the easier it is to manipulate it through sharp turns and small radius. A single layered dilating element is much more maneuverable than a double layered dilating element.

It is a primary objective of the present invention to provide a low-profile balloon catheter having a hybrid compliance curve that has a particular use in a medical procedure.

Another objective of the present invention is to provide a method for manufacturing a single layered balloon catheter having a hybrid compliance curve.

Another objective of the present invention is to provide a single layer balloon catheter, having a high compliance curve in the lower inflation range and a low compliance curve in the higher inflation range, that together combine to provide a hybrid compliance curve.

Still another objective of the present invention is to provide a balloon catheter that has a high compliance curve in the lower inflation range and a low compliance curve in the higher inflation range and is reversible through multiple inflations within the lower inflation range.

SUMMARY OF THE INVENTION

To achieve these and other objectives, the present invention provides a new and unique single layer balloon catheter and method of producing the unique single layer balloon catheter that causes the balloon to have a hybrid compliance curve.

A preferred embodiment of the present invention includes a single layered balloon, that is molded from a polymeric material to a specific nominal diameter, the balloon is then shrunk to a diameter that is less than the original diameter. The resulting shrunk balloon has a high compliance curve when inflated and stretched from its shrunk diameter to a diameter that is approximately equal to its original specific diameter. The balloon catheter can be subjected to multiple inflation-deflation cycles and it will maintain its high compliance curve provided it is not inflated sufficiently to extend into the non compliant portion of its hybrid compliance curve. When the balloon catheter has been expanded to a diameter that is approximately equal to its original diameter, then further inflation of the balloon will result in its expansion following a non-compliant curve. As a result such a balloon catheter has a hybrid compliance curve. However, once the balloon has reached its non compliant phase its compliant characteristics have been lost. If such a balloon is deflated and then reinflated it will follow a non compliant compliance curve during its entire expansion.

An important advantage of the present invention is that a physician can select a low profile balloon catheter that will perform certain desired functions when located in the vascular system and inflated to particular pressures that cannot be performed with currently available balloon catheters.

It is another advantage of the present invention that a physician will have a greater variety of balloon catheters to choose from that will have the capability to perform new functions or combinations of functions that formally required multiple balloon catheters.

These and other objects and advantages of the present invention will no doubt become apparent to those skilled in the art after having read the following detailed description of the preferred embodiment which are contained in and illustrated by the various drawing figures.

DETAILED DESCRIPTION OF THE PREFERRED EMBODIMENT

Figure 1A:
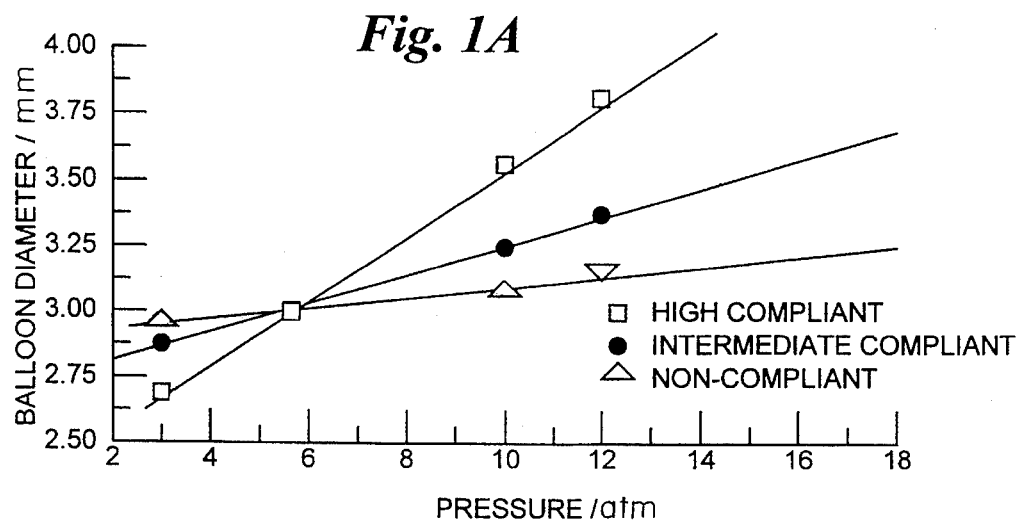
FIG. 1A is a graph showing compliance curves for several dilating catheters with the diameter of the balloon, measured in millimeters, as the ordinate and inflating pressure, measured in atmospheres, as the abscissa.
Figure 2A:
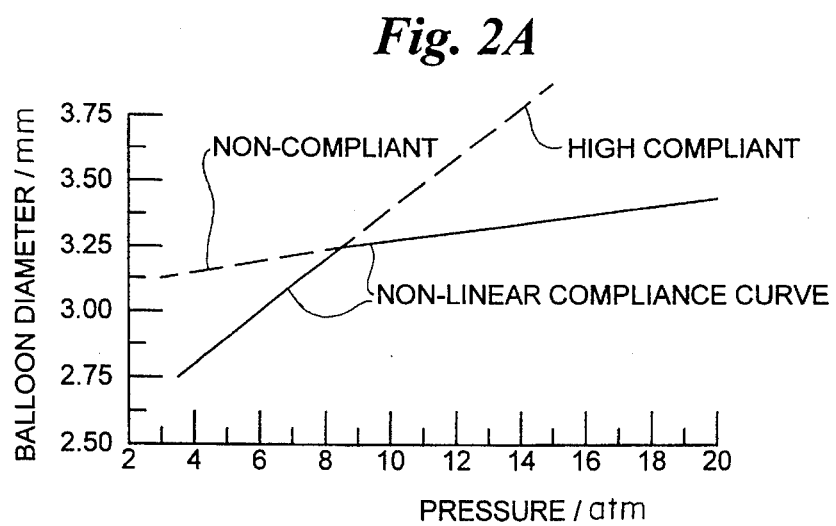
FIG. 2A is a graph, with balloon Diameter measured in millimeters as the ordinate and inflating pressure measured in atmospheres as the abscissa, on which is shown the compliance curve for two different balloons and also the combined hybrid compliance curve.
Figure 3:
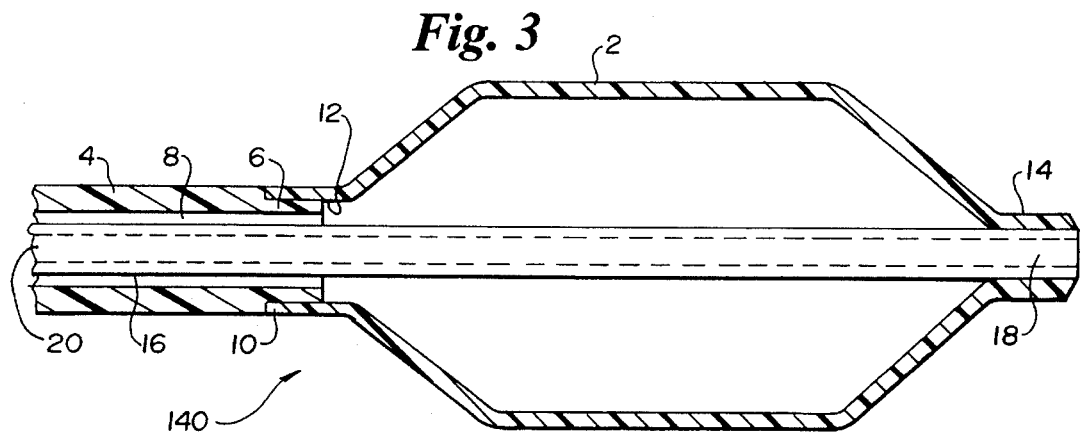
FIG. 3 shows a dilation catheter in cross-section including a balloon having a hybrid compliance curve.

The present invention will be illustrated and described as an over-the-wire balloon catheter for use in angioplasty of the type illustrated in FIG. 3. However it should be understood that the present invention can be applied to fixed-wire catheters including shortened guide wire lumens or to non-over-the-wire balloon catheters. Furthermore this invention can be used in balloon catheters intended for use in any and all vascular systems or cavities of the body.

Referring to FIG. 3 which shows the distal end of a balloon catheter 140. The balloon catheter 140 illustrated in FIG. 3 is an example of the type of catheter that the subject invention can be applied to but it should be understood that the invention can be applied to any type of balloon catheter. Furthermore, although several embodiments of balloon catheters having hybrid compliant curves will be disclosed herein their visual appearance is the same, in fact their visual appearance is no different than current balloon catheters. The balloon 2 is constructed of material such as poly(ethylene terephthalate) which is referred to as a PET balloon. Conventional balloon catheters made from PET have a low compliant compliance curve. The catheter is made up of an elongated outer plastic tube 4 having a distal end 6. The plastic tube 4 is preferably made of a flexible material such as a high density polyethylene. The elongated outer plastic tube 4 has a lumen 8 that functions as the inflation lumen and extends its entire length. There is a recessed area 10 at the distal end 6 into which the proximal end 12 of the balloon 2 is secured by bonding. The balloon 2 is molded to a desired shape, size and wall thickness. The shape of balloon 2 is generally cylindrical with reduced portions at each end. The proximal end 12 of balloon 2 is bonded to the recessed area 10 formed in the distal end 6 of the elongated outer plastic tube 4.

An elongated inner tube 16 is concentric with and within the elongated outer plastic tube 4. The inflation lumen 8 is defined by the inner surface elongated outer plastic tube 4 and the outer surface of elongated inner tube 16. The distal end 18 of elongated inner tube 16 extends distally of the distal end 6 of elongated outer tube 4. The distal end 14 of balloon 2 is adjacent to the distal end 18 of the elongated inner tube 16 and is secured thereto by bonding. The elongated inner tube 16 is hollow and thus forms a guide wire lumen 20. Since the un-inflated diameter of an angioplasty balloon is generally greater than the diameter of the outer plastic tube 4 it is the usual practice to fold down the balloon and wrap it in the folded condition such that it will maintain a low-profile during un-inflated use. Balloon catheters having a low profile are easier to manipulate through the patients vascular system and is particularly beneficial when passing the balloon through a tightly closed lesion.

The process for making a balloon for a balloon catheter than will have the hybrid compliance curve of this invention includes three major process; extruding of a tube, blow molding the balloon and annealing the balloon. Each of these major process include a number of process steps.

Polyethylene terephalate (PET) homopolymers and copolyesters can be used as the extrusion material. The copolyesters can be synthesized from ethylene glycol and a mixture of dimethyl terephthalate and dimethyl isophthalate by a two-step ester interchange process. The copolyesters can be branched via trifunctional compounds. The composition of the third component is in the range of 0.001%–40%. The following, Table I, provides physical properties of the homopolyester and copolyesters used in the extrusion process.

TABLE I

| Physical properties of PET Homopolymer and Copolymers | | | | |
|---|---|---|---|---|
| | HOMO- | COPOLYESTERS | | |
| Properties | POLYMER | I | II | III |
| Ratio of terephthalate to isophthalate | 100/0 | 97/3 | 92/8 | 87/13 |
| Intrinsic viscosity | 0.72 | 0.80 | 0.80 | 0.68 |

TABLE I-continued

| Physical properties of PET Homopolymer and Copolymers | | | | |
|---|---|---|---|---|
| | HOMO- | COPOLYESTERS | | |
| Properties | POLYMER | I | II | III |
| Melting T °C. | 250 | 248 | 230 | 221 |

The polyethylene terephthalate homopolymers and copolymers resins are dried by a hot air dryer using −40° Fahrenheit dew point air in a plenum style hopper. The polymer moisture content is controlled within a range of 1 to 90 parts per million by varying the drying temperature and time.

The extruding machine has a length to diameter ratio of 20:1 and has a minimum of three temperature control zones and additional heater zones for the adapter, head and die. The temperature controllers are of the proportioning type that can maintain temperatures within precise limits to thereby provide a homogeneous melt. The materials from which the barrel and screw components of the extrusion machine are conventional bimetallic, surface hardened and chrome plated. A conventional screw with a 3:1 compression ratio and a relatively constant transition from feed to metering zone has been successfully used in the process. However a costumed designed screw has been designed to improve the melt uniformity and mixing without excessive shear or polymer degradation. The extrusion machines breaker plate, adapter, head and tooling have been designed such that they provide gradual transitions, rounded edges and a minimum of obstructions. Screen packs of 60-80-60 and 60-1400-60 meshes have been found to generate adequate back pressure. The die and tip drawdown ratios are maintained between 2:1 and 3:1 and the die land lengths are 10 to 20 times the part wall thickness. Sizing of the tube is accomplished by free extrusion while maintaining constant nitrogen pressure inside the tubing while being quenched in a conventional water bath at ambient temperatures. Specific extrusion parameters that were used to extrude tubes from which balloons having hybrid compliance curves in accordance with this invention are listed in Table II.

TABLE II

| Polymer Types | Temperature °C. | | | | | | Melting | |
|---|---|---|---|---|---|---|---|---|
| | Zone 1 | Zone 2 | Zone 3 | Zone 4 | Zone 5 | Zone 6 | Pressure | Temperature |
| PET | 275 | 272 | 267 | 259 | 258 | 275 | 2900 psi | 272° C. |
| PET | 244 | 254 | 260 | 261 | 259 | 260 | 3017 psi | 265° C. |
| Co I | 248 | 249 | 249 | 249 | 248 | 265 | 4100 psi | 258° C. |
| Co II | 244 | 243 | 243 | 244 | 244 | 257 | 6600 psi | 254° C. |
| Co III | 229 | 232 | 233 | 233 | 227 | 230 | 4800 psi | 242° C. |

The process for molding or blowing a dilation catheter balloon that can be used to incorporate this invention will be discussed with reference to FIG. 4. This discussion will describe the process for producing a specific dilation catheter balloon, thus the material from which it is made, its dimensions and specific temperatures and time periods used in the process will be included in the example. However it should be understood that this explanation relates to a specific balloon and the invention is not limited to this specific example. It should also be noted that the specific balloon discussed with reference to FIG. 4 could be used in the construction of a balloon catheter of the type illustrated in FIG. 3 or other types of balloon catheter.

This invention has been applied to balloons made from polyethylene terephalate (PET) homopolymers and copolyesters. The copolyesters used in these balloons can be synthesized from ethylene glycol and a mixture of dimethyl terephthalate and dimethyl isophthalate. Copolyesters can be branched via trifunctional compounds. The composition of the third compound is the range of 0.001%–40%. The Intrinsic viscosity (IV) of the PET homopolymer material was 0.72 and for the copolyesters 0.68 and 0.80.

The process begins with a length of extruded tube, about 20 centimeters long, made from the balloon material. Balloons formed from the extruded tubes as they exist after extrusion have been successfully processed to incorporate this invention of a balloon catheter having a hybrid compliance curve. However the tube as it is received from the extrusion process can be pre stressed or stretched prior to subjecting it to the blow molding process.

When it is desired to stretch the extruded tube, the starting tube is stretched to 1.5–3.0 times its initial length while submerged in water at a temperature of 90° Centigrade. The preferred stretching ratio is 2.25. This stretching of the starting tube contributes further to the orientation of the molecules along the length of the tube. It is preferred to mold the balloon soon after the tube has been extruded, to insure that conditions of the tube, such as moisture content remain acceptable.

Figure 4:
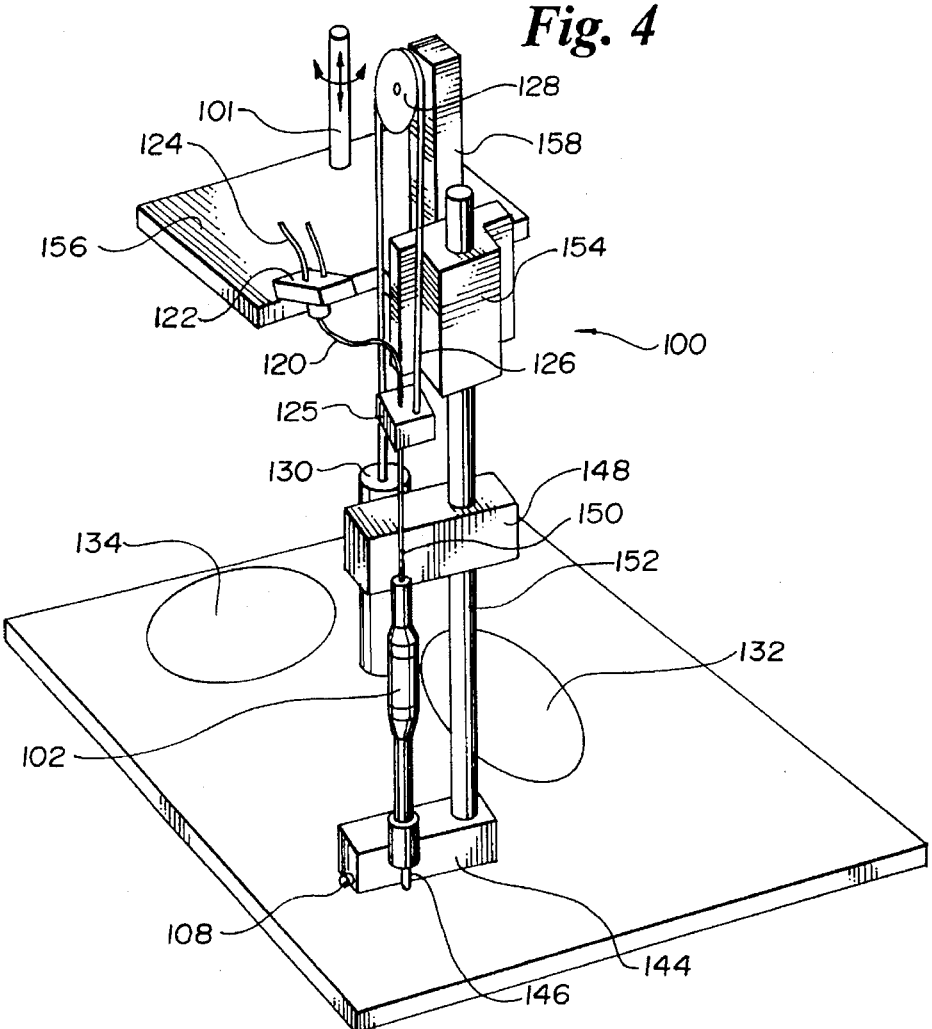
FIG. 4 shows the machine used to form the balloon used to produce a balloon catheter in accordance with this invention.

The apparatus or blowing machine 100 shown in FIG. 4 receives the balloon mold 102 and supports and manipulates it through the balloon forming process. The blowing machine 100 is supported by an arm 101 that can be reciprocated vertically and oscillated, as indicated by the arrows. The blowing machine 100 includes a lower mold gripper 144 that has a channel 146 and an upper mold gripper 148 that has a channel 150. The upper and lower mold grippers 148 and 144 are secured to a vertical shaft 152 that is secured at its upper end to a locking device 154 which is mounded on a frame member 156. This movement enables the mold 102 to be indexed to a location over a hot water tank 132 and then a quenching tank 134 and submerged in these tanks for specific time periods. It should be noted that although the tanks 132 and 134 are filled with water at the appropriate temperature this operation can also be performed with air at the appropriate temperature. The movement imparted to arm 101 can be controlled by an computer controlled device, which is not considered to be a part of this invention.

Figure 5:
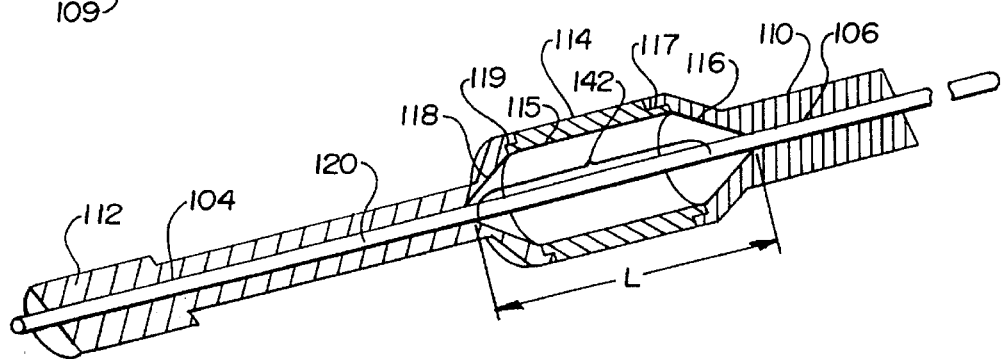
FIG. 5 shows the balloon mold used in the machine shown in FIG. 4.

The stretched tube 120 is placed in the mold 102, which as can be best seen in FIG. 5 is a three part mold. Mold 102 includes an upper mold portion 110, a lower mold portion 112 and a central mold portion 114. The upper mold portion 110 has an upper diverging section 116 and a cylindrical section 106. The lower mold portion 112 has a lower diverging section 118 and a cylindrical section 104. The diameter of the cylindrical sections 104 and 106 being slightly larger than the diameter of the stretched tube 120 that is to be placed in the mold. The upper and lower mold portions 110 and 112 are counterbored at 117 and 119 respectively. The central mold portion 114 has a cylindrical section 115 that has a diameter corresponding to the nominal diameter of the balloon to be produced by the mold. The central mold portion 114 has a reduced outer diameter area at both ends that are received in counterbores 117 and 119 to thereby connect the three parts of the mold together.

Alternatively, both end portions of the stretched tube 120 are then stretched further, leaving a central section 142 (see FIG. 5) that has not been subjected to this further stretching. The length of the central section 142 is slightly less then the distance L, identified in FIG. 5, which extends from the juncture of the diverging section 116 with the cylindrical section 106 to the juncture of the diverging section 118 with the cylindrical section 104. This further stretching of the tube 120 has caused the central section 142 to have a wall thickness that is greater than the end portions of the tube. As shall be discussed later, during the balloon blowing step an upward force is exerted on the tube 120 causing it to be stretched in the longitudinal direction.

The further stretched tube 120 is placed in the three part mold 102 such that it fits snugly in the upper 110 and lower 112 tube portions and extends along the axis of the central balloon portion 114. The tube 120 is placed in the mold such that the bottom edge of the central section 142 is at the intersection of the lower diverging portion 118 and the cylindrical section 104 of the mold. Since the length of the central section 142 is slightly shorter than the length L, the upper edge of the central section 142 will be below the intersection of the upper diverging portion 116 with the cylindrical section 106.

Figure 6:
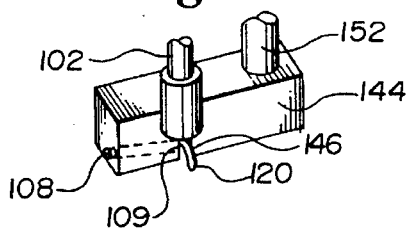
FIG. 6 is an enlarged view of the lower mold gripper that includes details not visible in FIG. 4.

The mold is then secured to the molding machine 100 by placing the upper end of the mold in the upper mold gripper 148 with the tube lying in the channel 150 and the lower end of the mold in the lower mold gripper with the tube 120 lying in the channel 146. As can be best seen in FIG. 6, the lower mold gripper 144 has a clamping device 108 that includes a point 109. When the clamping device 108 is closed point 109 presses the tube 120 against the surface of channel 146 to prevent gas from leaking out this end of the tube 120.

A connector 122, supported by the frame 156, is provided for connecting the upper free end of tube 120 to a source of pressurized gas 124 such as Nitrogen. The pressure source 124 can apply a force up to 300 psi internally of tube 120. However a force of 200–270 psi is used most often. The tube 120 extends through and is griped by lifting block 125 which is located between the upper end of mold 102 and the connector 122. The section of tube 120 that extends from lifting block 125 to connector 122 is provided with a slight amount of slack for a purpose to be discussed. The lifting block 125 functions to exert an upward force on the tube 120 in such a way that the internal passage through tube 120 remains open and is not collapsed. The upward force can be applied to the lifting block, for example, by connecting a wire 126 to the lifting block 125, extending the wire over a pulley 128, and connecting a weight 130 to the free end of wire 126. A 50 gram weight has been used in the preferred embodiment of the blowing machine, however the actual amount of this weight would be a factor of the size of the balloon and starting tube. The pulley 128 is mounted for rotation on a post 158 that extends upwardly from the frame 156.

The arm 101 then indexes the blowing machine 100 horizontally so that it overlies the hot water tank 132 and then dips the mold 102 into the tank 132 which contains water at about 95° Centigrade. In the preferred process the bottom half of the mold is first submerged for a 15 second period and then the entire mold is submerged for an additional 40 seconds. Pressure is applied to the interior of tube 120 through pressure source 124 during the time period that the mold is submerged in the hot water. A pressure in the range of 100–300 psi, with a preferred range of 200–270 psi is applied. The internal pressure causes the tube 120 to expand radially in the central balloon portion 114 of the mold. The diameter of the tube 120 expands in a range of 3–10 times its original diameter however the preferred ratio is in the range of 6–9 times its original diameter. Although most of the expansion during this step of the process occurs in the radial direction some additional longitudinal stretching also occurs. This longitudinal stretching is a factor of the upward force applied to the tube by the weight 130. During this phase of the process the lifting block 125 visually moves upward relative to the top end of mold 102. This upward movement pulls the upper end of tube 120 upwardly out of the upper end of mold 102 and causes the upper edge of the central section 142 to move upwardly such that it is at the intersection of the upper tube portion 110 and the upper diverging portion of the mold. As a result the expanded balloon is formed from the central section 142 which had a greater wall thickness than the end portions of tube 120 prior to blowing the balloon. After the balloon has been blown the wall thickness of the end portions and the balloon portion has been reduced as a result of the expansion that has occurred. The upward movement can be accommodated by the slack that was left in the section of tube 120 that extends from lifting block 125 and the connector 122.

The entire mold is then removed from the 95° Centigrade water bath, indexed horizontally until it overlies quenching tank 134. The entire mold 102 is then dipped into and quench, in room temperature water, for about 10 seconds.

The blowing machine 100 is then removed from the room temperature quench, the mold 102 is released from the blowing machine 100 and opened up. The formed balloon is then released and removed from the mold 102. The free ends of the balloon are then trimmed and the balloon catheter is assembled. An assembled over-the-wire type balloon catheter 140, is illustrated in FIG. 3.

The final process that the assembled balloon catheter must undergo is the annealing technique. The entire balloon catheter is submerged in water or air at a temperature in the range of 25°–100° Centigrade for 3– 180 minutes. The preferred temperature range being 65°– 80° Centigrade. It should be understood that the temperature and time required in this annealing process, depends upon the size of the balloon that is being processed. This annealing process causes the length and the diameter of the balloon to decrease and the wall thickness to increase. After the balloon catheter has been removed from the annealing process it is sterilized under ethylene oxide at 47° Centigrade.

Figure 7:
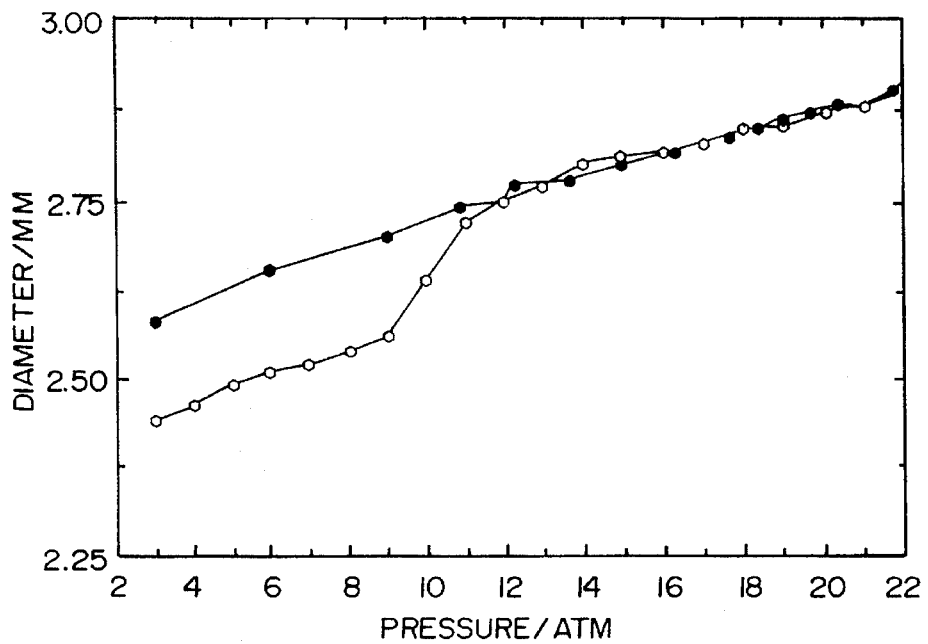
FIG. 7 is a graph, with balloon Diameter measured in millimeters as the ordinate and inflating pressure measured in atmospheres as the abscissa, in which compliance curves of a balloon made in accordance with this invention is plotted.

FIG. 7 is a graph, with pressure in atmospheres plotted on the X axis and Diameter in millimeters plotted on the Y axis, of a balloon that has been manufactured in accordance with this invention. The balloon used for this graph had an original nominal diameter before being shrunk of 2.75 millimeters. The curve formed by connecting the circles is the compliance curve for the shrunk balloon when it is originally inflated. This compliance curve, at pressures less than 12 atmospheres, is relatively steep and has the characteristics of a high compliant compliance curve. The section of this curve above 12 atmospheres has a very shallow pitch which is characteristic of a non compliant compliance curve. The curve in FIG. 7, that is formed by connecting the solid dots, is the compliance curve of the same balloon after it has been deflated from a pressure above 12 atmospheres and then reinflated. This second compliance curve has the same pitch throughout its entire extent that the earlier discussed curve had above 12 atmospheres. Thus it is apparent that the balloon having been once inflated above 12 atmospheres has lost its compliant characteristics, and when reinflated it follows a non compliant compliance curve rather than a hybrid compliance curve.

Figure 8:
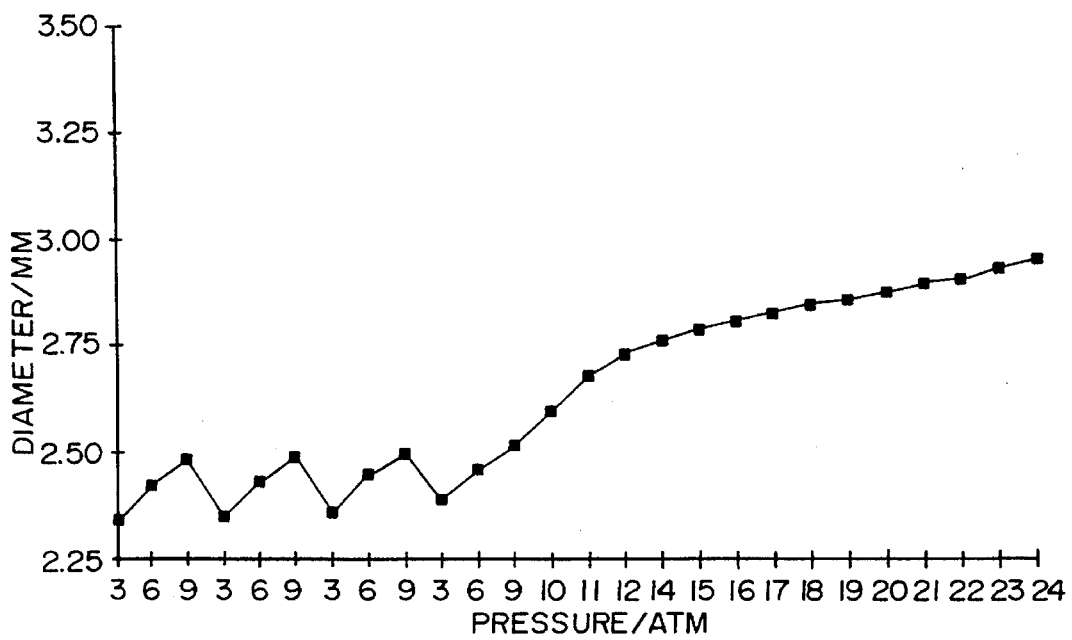
FIG. 8 is a graph, of a balloon made in compliance with this invention in which the balloon diameter measured in millimeters is plotted as the ordinate and inflating pressure measured in atmospheres as the abscissa. The balloon used for this graph was inflated and its diameter measured at 3, 6 and 9 atmospheres and then the balloon was deflated and the process repeated several times. The fourth inflation was continued to 24 atmospheres.

Referring now to the graph shown in FIG. 8, in which pressure in atmospheres is plotted on the X axis and balloon diameter in millimeters is plotted on the Y axis. The compliance curve of a balloon that has been manufactured in accordance with this invention has been plotted on this graph. The balloon plotted on this graph, like the balloon used for the FIG. 7 had a nominal diameter prior to being shrunk of 2.75 millimeters. In collecting the data for this graph the pressure in the balloon was increased and the diameter measured at 3, 6 and 9 atmospheres. The balloon was then deflated and the process of increasing the pressure and recording the diameter at 3, 6 and 9 atmospheres was repeated. The balloon was then deflated again and the process of inflating and recording the diameter was repeated a third time. Once more the balloon was deflated and the process of inflating and recording the diameter was began a fourth time. However on the fourth cycle the pressure was increased and the diameter recorded up to 24 atmospheres. The balloon displayed the characteristics of a compliant balloon in each of the four inflations up to 9 atmospheres and then followed a non compliant compliance curve when in the fourth inflation the pressure was increased above 12 atmospheres.

Figure 9:
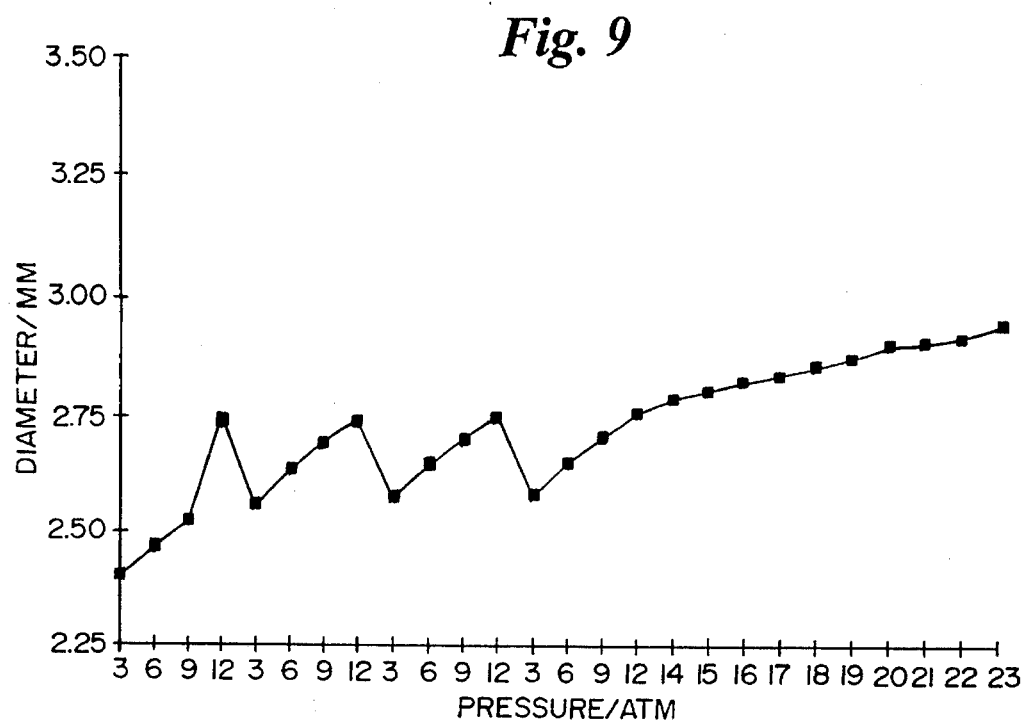
FIG. 9 is a graph, of a balloon made in compliance with this invention in which the balloon diameter measured in millimeters is plotted as the ordinate and inflating pressure measured in atmospheres as the abscissa. The balloon used for this graph was inflated and its diameter measured at 3, 6, 9 and 12 atmospheres and then the balloon was deflated and the process repeated several times. The fourth inflation was continued to 23 atmospheres.

Referring now to the graph shown in FIG. 9, in which pressure in atmospheres is plotted on the X axis and balloon diameter in millimeters is plotted on the Y axis. The compliance curve of a balloon that has been manufactured in accordance with this invention has been plotted on this graph. The balloon plotted on this graph, like the balloon used for the FIGS. 7 and 8 had a nominal diameter prior to being shrunk of 2.75 millimeters. In collecting the data for this graph the pressure in the balloon was increased and the diameter measured at 3, 6, 9 and 12 atmosphere. The balloon was then deflated and the process of increasing the pressure and recording the diameter at 3, 6, 9 and 12 atmosphere was repeated. The balloon was then deflated again and the process of inflating and recording the diameter was repeated a third time. Once more the balloon was deflated and the process of inflating and recording the diameter was began a fourth time. However on the fourth cycle the pressure was increased and the diameter recorded up to 23 atmospheres. The balloon displayed the characteristics of a compliant balloon in each of the four inflations up to 12 atmospheres and then followed a non compliant compliance curve when in the fourth inflation the pressure was increased to 22 atmospheres.

The graphs of FIGS. 8 and 9 illustrate that balloon manufactured in accordance this invention have reversible compliant characteristics provided they are not inflated beyond the nominal diameter that they had prior to shrinking.

Figure 10:
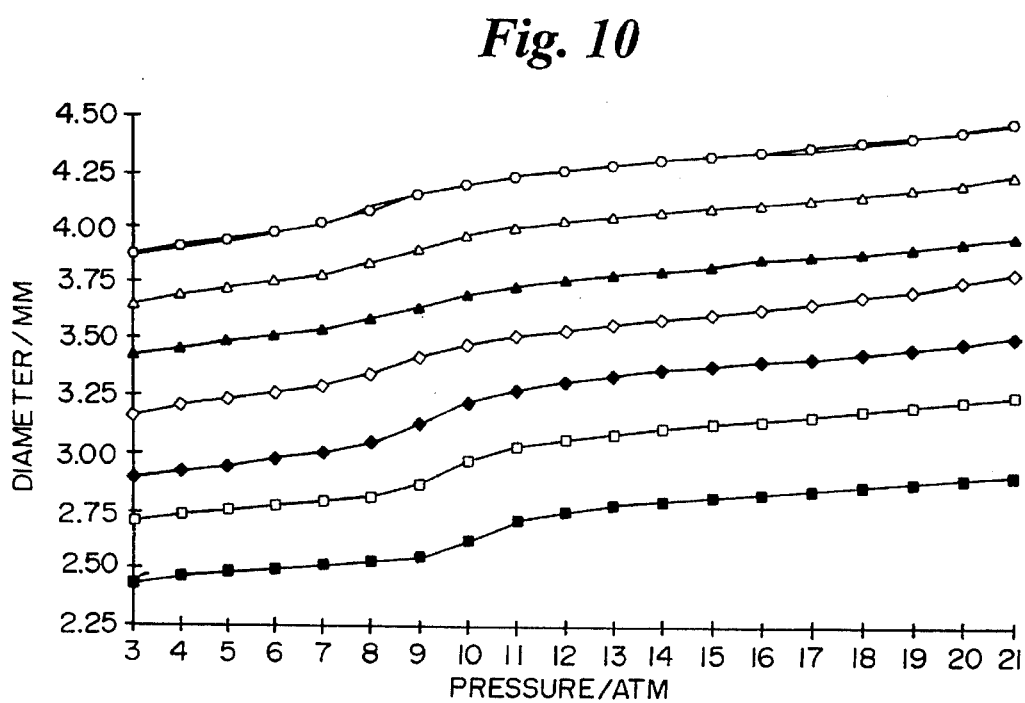
FIG. 10 is a graph, with balloon diameter measured in millimeters as the ordinate and inflating pressure measured in atmospheres as the abscissa, in which the compliance curves of a series of balloons manufactured in accordance with this invention have been plotted.

Referring now to FIG. 10 which is a graph, with pressure in atmospheres plotted on the X axis and diameter in millimeters plotted on the Y axis. The compliance curves of a series of balloons, having pre shrunk nominal diameters from 2.75 millimeters to 4.25 millimeters, that has been manufactured in accordance with this invention are plotted on this graph. An individual symbol such as a solid square or an outline of a triangle have been used to identify the data points for each curve in the series. Although the extruded tubes from which these individual balloons were blown and the resulting balloon wall thicknesses were not the identical, the resulting compliance curves are all similar and all are nonlinear.

Although the present invention has been described in terms of specific embodiments, it is anticipated that alterations and modifications thereof will no doubt become apparent to those skilled in the art. It is therefore intended that the following claims be interpreted as covering all such alterations and modifications as fall within the true spirit and scope of the invention.

I claim:

1. A method of producing a balloon catheter including a single layered balloon made from non compliant material such that the balloon will have a hybrid compliance curve, comprising the steps of:

(a) placing an elongated tube made of non compliant material into a balloon blow mold;

(b) constraining a first end of the elongated tube in the balloon blow mold and restricting the flow of fluid through said first end of the tube;

(c) submerging the balloon blow mold in water at about 95° Centigrade and applying pressure to the interior of the elongated tube sufficient to expand the tube such that the tube expands diametrically to thus form a balloon having a specific diameter;

(d) removing the balloon blow mold from the water after it has been submerged for about 45 seconds and submerging it in water at room temperature;

(e) removing the balloon blow mold from the room temperature water after about 10 seconds;

(f) removing the balloon from the balloon blow mold and using it to assemble a balloon catheter;

(g) submerging the balloon catheter in water or air at 30°–80° Centigrade for from 1 to 50 minutes to thereby shrink the balloon to a diameter that is less than its specific diameter.

2. The invention as set forth in claim 1 wherein prior to placing the elongated tube into the balloon blow mold the tube is formed by an extrusion process.

3. The invention as set forth in claim 2 in which the extruded elongated tube is stretched in water at about 90° Centigrade for a range of 5–15 seconds, prior to placing it in the balloon blow mold.

4. The invention as set forth in claim 3 in which the extruded elongated tube is stretched to about 2.25 times its original length.

5. The invention as set forth in claim 2 in which the extruded elongated tube is stretched to about 2.25 times its original length, prior to placing it in the balloon blow mold.

6. The invention as set forth in claim 1 wherein prior to step (c) a force is applied to the other end of the tube in a direction away from said first end.

7. The invention as set forth in claim 1 wherein prior to step (a) both ends of the elongated tube are stretched leaving an un-stretched section between the stretched ends that has a length that is less than the length of the balloon to be formed and which un-stretched section is expanded into the balloon.

8. The invention as set forth in claim 7 wherein when performing step (b) said first end of the elongated tube is constrained in the balloon blow mold such that the end of the un-stretched section that corresponds to said first end coincides with the end of the balloon cavity formed in the balloon blow mold.

9. The invention as set forth in claim 8 wherein the pressure applied to the interior of the elongated tube in step (c) in combination with the force being applied to the tube in a direction away from said first end elongates the un-stretched section in the longitudinal direction and further orientates its molecules in the longitudinal direction.

* * * * *